United States Patent
Kwon

(10) Patent No.: US 9,295,536 B2
(45) Date of Patent: Mar. 29, 2016

(54) AUTOMATIC ROTATING INTERDENTAL BRUSH

(71) Applicant: KOEL CO., LTD., Ansan-si (KR)

(72) Inventor: O-Dae Kwon, Gimpo-si (KR)

(73) Assignee: KOEL CO., LTD. (KR)

( * ) Notice: Subject to any disclaimer, the term of this patent is extended or adjusted under 35 U.S.C. 154(b) by 0 days.

(21) Appl. No.: 14/533,331

(22) Filed: Nov. 5, 2014

(65) Prior Publication Data

US 2015/0135451 A1 May 21, 2015

(30) Foreign Application Priority Data

Nov. 15, 2013 (KR) .......................... 10-2013-0138860

(51) Int. Cl.
| | |
|---|---|
| *A46B 13/08* | (2006.01) |
| *A61C 17/32* | (2006.01) |
| *A61C 17/26* | (2006.01) |
| *A61C 15/00* | (2006.01) |

(52) U.S. Cl.
CPC .................. *A61C 17/26* (2013.01); *A46B 13/08* (2013.01); *A61C 15/00* (2013.01); *A61C 17/32* (2013.01); *A46B 2200/108* (2013.01)

(58) Field of Classification Search
CPC ................................. A46B 13/08; A61C 17/32
See application file for complete search history.

(56) References Cited

U.S. PATENT DOCUMENTS

| 2,636,393 | A | * | 4/1953 | Josephs | 74/89.45 |
| 3,947,910 | A | * | 4/1976 | Akerman | 15/27 |
| 2012/0167910 | A1 | * | 7/2012 | Weigel | 132/218 |
| 2014/0373293 | A1 | * | 12/2014 | Liao | 15/143.1 |

FOREIGN PATENT DOCUMENTS

| JP | 11113930 | 4/1999 |
| JP | 2002253346 | 9/2002 |
| KR | 200121472 | 4/1998 |
| KR | 1020010011588 | 2/2001 |
| KR | 1020040008970 | 1/2004 |
| KR | 200416243 | 5/2006 |
| KR | 100860090 | 9/2008 |

* cited by examiner

*Primary Examiner* — Randall Chin
(74) *Attorney, Agent, or Firm* — Cantor Colburn LLP

(57) ABSTRACT

Provided is an automatic rotating interdental brush that automatically rotates a brush to efficiently clear away extraneous substances, plaque and the like trapped in between teeth by pushing and pulling a grip body while causing the brush to be in contact with the teeth. The automatic rotating interdental brush includes a body, a rotor that protrudes from and retracts into the body to rotate a brush, a brush coupled to the rotor, and a rotating unit for causing the rotor to protrude and retract while being rotated. The rotating unit includes a screw provided at a rear end of the rotor and having a spiral rotation guide groove longitudinally formed thereon, and a rotating guide hole formed in the body and having a shape corresponding to a cross-section of the screw so as to cause the screw disposed therein to be linearly moved while being rotated.

3 Claims, 3 Drawing Sheets

AUTOMATIC ROTATING INTERDENTAL BRUSH

BACKGROUND OF THE INVENTION

1. Field of the Invention

The present invention relates generally to an interdental brush that is used in clearing away extraneous substances, plaque and the like trapped in between teeth, and more particularly to an automatic rotating interdental brush that automatically rotates a brush to efficiently clear away extraneous substances, plaque and the like trapped in between teeth by pushing and pulling a grip body while causing the brush to be in contact with the teeth, and which can also serve as an ear-cleaning device for cleaning earwax by replacing the brush with a soft brush.

2. Description of the Related Art

As well known in the art, an interdental brush is used to efficiently clear away food remnants trapped in between teeth, scale, bacterial plaque and the like that is only marginally removed by a common toothbrush and to softly rub a gum.

As disclosed in Korean Unexamined Patent Publication No. 10-2001-0011588, titled "Interdental Brush", and Korean Patent No. 10-0468075, titled "Interdental Brush Containing Cleaning Liquid", an interdental brush is composed of a wire constructed from a pair of twisted wire elements, and bristles densely attached to the wire thus constituting a brush. In use, a user grasps a body of the interdental brush with his/her fingers, and disposes the brush including the bristles between teeth. Thereafter, the user repeatedly pushes the brush up and down or rotates the brush to clean interdental areas.

In this kind of conventional interdental brush, after the brush composed of bristles is inserted between teeth, the brush is repeatedly moved up and down or is rotated to move the bristles to be moved up and down by a user. In other words, the body of the interdental brush is repeatedly moved up and down within a short stroke range or is rotated to clean teeth by a user.

However, reciprocating the body of the interdental brush within a short stroke range or rotating the body of the interdental brush is a considerably cumbersome work and requires a long period of time. Furthermore, interdental cleaning effects are not sufficiently obtained without careful work.

In order to overcome the problems such as a cumbersome work of reciprocating or rotating a brush by hand, a prolonged cleaning time, a poor cleaning effect and the like, an interdental brush disclosed in Korean Utility Model Registration No. 20-0416243, titled "Electric Interdental Brush with Varying Folding Angle" is constructed in such a way that a battery and a motor are incorporated in a grip body, the motor is coupled to a brush and the brush is automatically rotated by the motor.

In Korean Utility Model Registration No. 20-0416243, titled "Electric Interdental Brush with Varying Folding Angle", since a brush is rotated to clean interdental areas by means of a motor by slightly pushing the brush against teeth, the interdental areas can be cleaned conveniently, quickly and efficiently without the need for user's carefulness.

However, the requirement of a battery and a motor increases manufacturing costs, and the battery must be frequently recharged or replaced. In addition, the risk of electric shock exists always.

SUMMARY OF THE INVENTION

Accordingly, the present invention has been made keeping in mind the above problems occurring in the prior interdental brush, and an object of the present invention is to provide an automatic rotating interdental brush that automatically rotates a brush to clean interdental areas merely by pushing and pulling a grip body back and forth without the use of a battery and a motor, thus providing the convenience in use, a prompt interdental cleaning and an improved cleaning effect.

Another object of the present invention is to provide an automatic rotating interdental brush in which components are simplified and are easily fabricated with each other so as to reduce manufacturing costs and improving productivity.

A further object of the present invention is to provide an automatic rotating interdental brush that allows various types of existing interdental brushes to be conveniently coupled thereto.

In order to accomplish the above object, the present invention provides an automatic rotating interdental brush, including: a body; a rotor that protrudes from and retracts into the body to rotate a brush; a brush coupled to the rotor; and a rotating unit for causing the rotor to protrude and retract while being rotated, wherein the rotating unit includes: a screw provided at a rear end of the rotor and having a spiral rotation guide groove longitudinally formed thereon; and a rotating guide hole formed in the body and having a shape corresponding to a cross-section of the screw so as to cause the screw disposed therein to be linearly moved while being rotated.

The body may include: a reception guide body accommodating the rotor and allowing the rotor to protrude therefrom and retract thereinto; and a rotating guide body coupled to a rear end of the reception guide body and having the rotation guide hole.

The rotor may include a coupling part at a front end thereof to allow the brush to be removably coupled thereto.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1A:
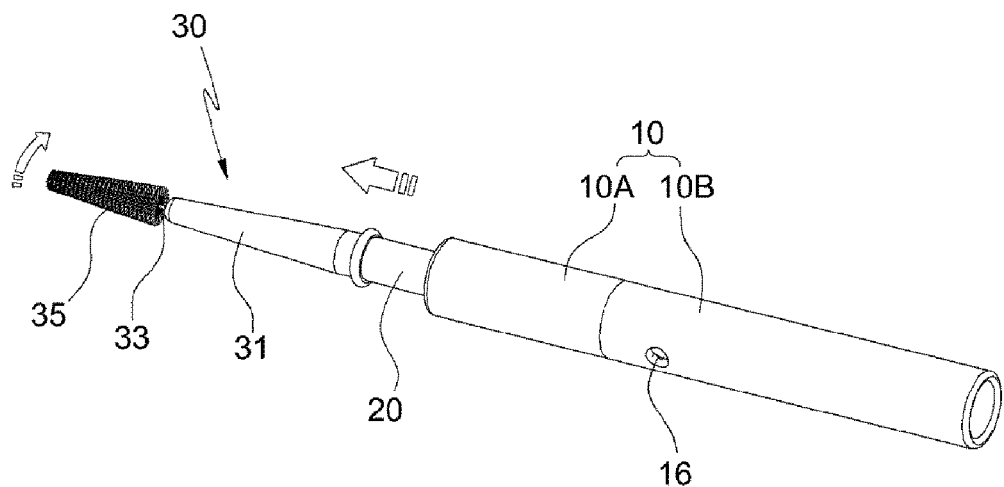
FIGS. 1A and 1B are a perspective view of an automatic rotating interdental brush according to the present invention.
Figure 1B:
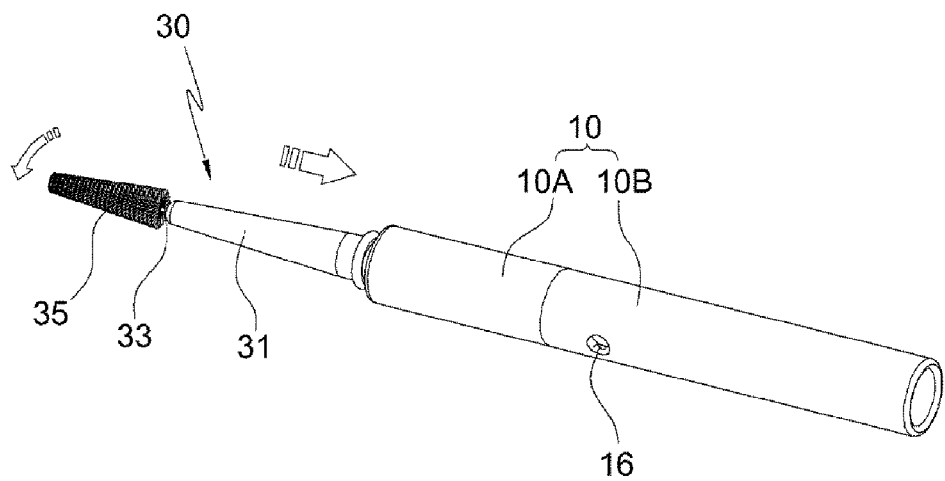
Figure 2:
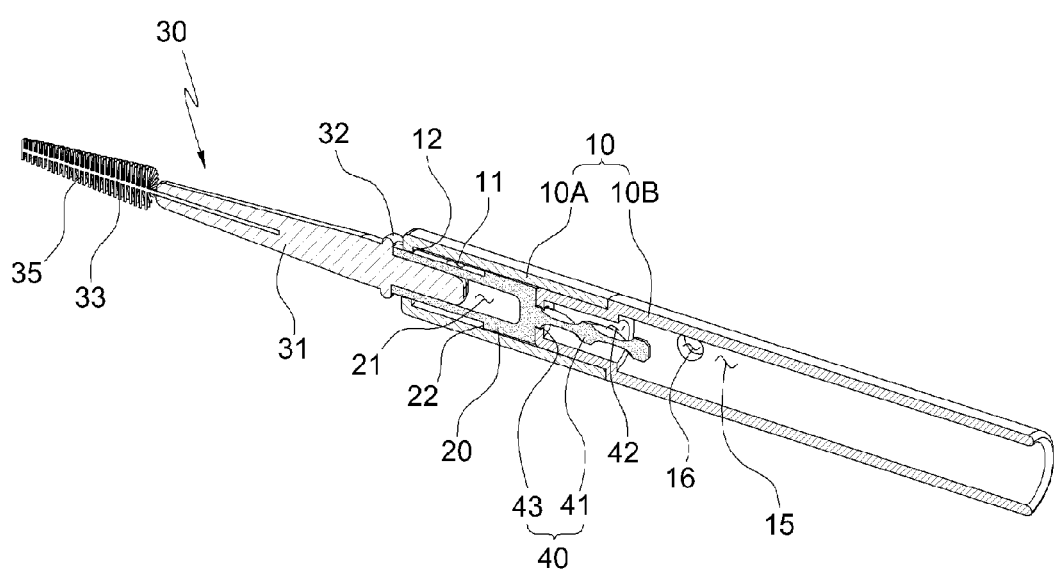
FIG. 2 is a perspective view of FIG. 1B which is longitudinally cut away.
Figure 3:
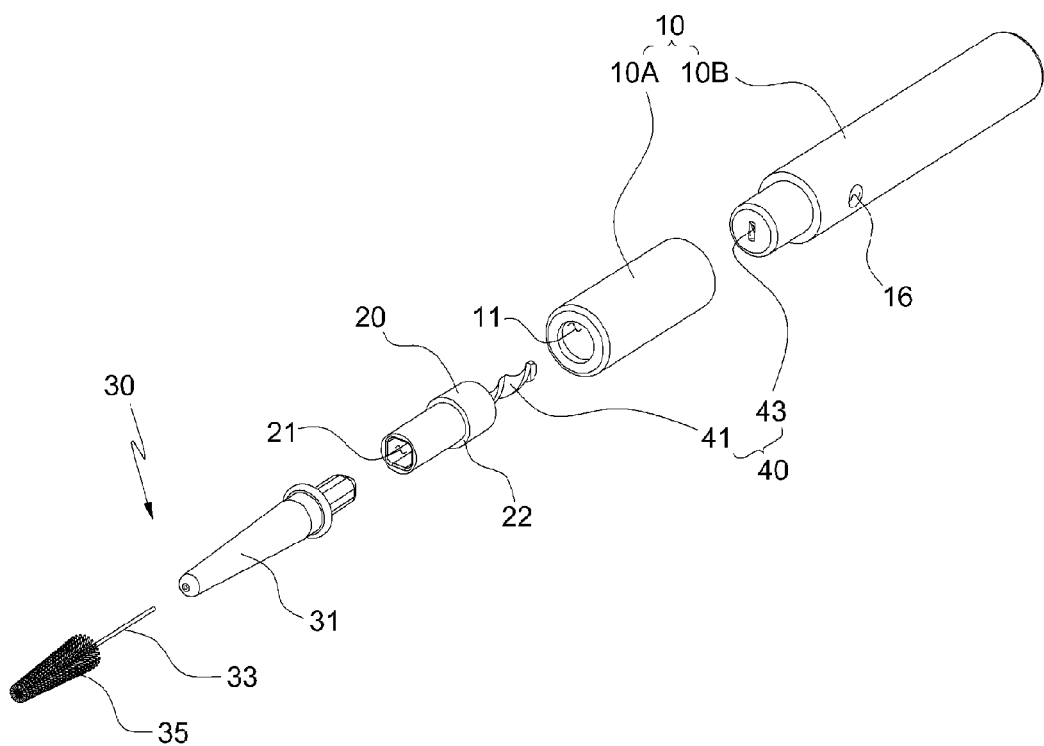
FIG. 3 is an exploded perspective view of FIGS. 1A and 1B.

Hereinafter, an automatic rotating interdental brush according to the present invention will be described in detail with reference to the attached drawings.

Prior to the detailed description of the present invention, the present invention will now be described in detail based on aspects (or embodiments). The present invention may, however, be embodied in many different forms and should not be construed as being limited to only the embodiments set forth herein, but should be construed as covering modifications, equivalents or alternatives falling within ideas and technical scopes of the present invention.

In the figures, like reference numerals, particularly, tens and units, or reference numerals having like tens, units and letters refer to like elements having like functions throughout, and unless the context clearly indicates otherwise, elements referred to by reference numerals of the drawings should be understood based on this standard.

Also, for convenience of understanding of the elements, in the figures, sizes or thicknesses may be exaggerated to be large (or thick), may be expressed to be small (or thin) or may be simplified for clarity of illustration, but due to this, the protective scope of the present invention should not be interpreted narrowly.

The terminology used herein is for the purpose of describing particular aspects (or embodiments) only and is not intended to be limiting of the present invention. As used herein, the singular forms are intended to include the plural forms as well, unless the context clearly indicates otherwise. It will be further understood that the terms "comprises," "comprising,", "includes" and/or "including," when used herein, specify the presence of stated features, integers, steps, operations, elements, and/or components, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which the present invention belongs. It will be further understood that terms used herein should be interpreted as having a meaning that is consistent with their meaning in the context of this specification and the relevant art and will not be interpreted in an idealized or overly formal sense unless expressly so defined herein.

As illustrated in the drawings, the automatic rotating interdental brush according to the present invention comprises several main components, that is, a body 10, a rotor 20, a brush assembly 30, and a rotating unit 40.

The body 10 is configured to be gripped by a user's hand, and is composed of a reception guide body 10A and a rotation guide body 10B.

The reception guide body 10A is provided therein with an internal space 11 that accommodates the rotor 20 and allows reception and retraction of the rotor 20. The reception guide body 10A is further provided at a front end thereof with an annular check protrusion 12 so as to prevent the rotor 20 from being separated therefrom.

The rotation guide body 10B includes a front section that is fitted in the internal space 11 through a rear end of the reception guide body 10A. A screw 41 of the rotating unit 40 passes through a front end of the rotation guide body 10B and is received in the rotation guide body 10B. The rotation guide body 10B includes a reception space 15 for reception and storage of a brush assembly 30. The rotation guide body 10B is formed with a vent hole 16 that allows the reception space 15 to communicate with the outside for ventilation of the reception space 15 and which functions to inhibit propagation of bacteria in bristles 35 of the brush assembly 30 accommodated in the reception space 15. The rotation guide body 10B is provided at a front end thereof with a rotation guide hole 43 having a shape corresponding to a cross-section of the screw 41 so as to cause the screw 41 to be moved while being rotated.

The rotor 20 is received in the internal space 11 of the reception guide body 10A and moves back and forth in the internal space 11 such that the front end of the rotor 20 protrudes from and retracts into the internal space 11. At this point, the rotor 20 is rotated by means of the rotating unit 40 during the protruding and retracting motions thereof, thus rotating the brush assembly 30.

The rotor 20 is provided on an outer surface thereof with a shoulder 22 that is caught by the annular check protrusion 12 of the reception guide body 10A thus preventing the separation of the rotor 20. The rotor 20 is further provided in a front section thereof with a coupling part 21 in which a brush body 31 of the brush assembly 30 is removably fitted.

The rotor 20 may be manufactured to be integrally formed with the brush assembly 30. In this case, when the bristles 35 is completely worn away, a user has to replace the worn bristles 35 with a new one thus increasing the maintenance costs. Accordingly, in order to reduce the maintenance costs in such a manner as to purchase only a new brush assembly 30 while using the existing components such as the rotor 20, the rotor 20 is provided at the front end thereof with the coupling part 21 to allow the brush body 31 to be removably coupled thereto in a convenient manner.

Thanks to the provision of the coupling part 21, any of the existing interdental brushes available in the market may be conveniently fitted in the coupling part 21 and then be used.

The coupling part 21 may be configured to have various shapes. As illustrated in the drawings, the coupling part 21 may be configured to have a polygonal inner surface such that the brush body 31 of the brush assembly 20 is fitted in the coupling part 21 in an interference fit manner. In this regard, since bodies of existing automatic rotating interdental brushes have somewhat different thicknesses, shapes and the like depending on a maker or a product model, it is preferable that the coupling part includes a plurality of inner surface sections having internal diameters that decrease in a stepwise fashion.

In addition to the configuration of the coupling part 21 in which the brush body 31 is fitted in an interference manner as shown in the drawings, the coupling part 21 may be configured such that the front part of the rotor 20 is longitudinally split into a plurality of segments that are annularly arranged to have an internal space for receiving a brush body and the longitudinal segments resiliently grasp an outer surface of the brush body fitted in the internal space.

The brush assembly 30 comprises a wire 33, bristles 35 densely attached to a front section of the wire 33, and a brush body 31 in which a rear section of the wire 33 is fitted.

The wire 33 is composed of a pair of wire elements that are twisted. The bristles 35 are attached to the wire 33 during the twisting procedure of the wire 33.

The brush body 31 is provided on an outer surface thereof with an external annular protrusion 32 that functions to restrict a length of the portion of the brush body 31 that is fitted into the coupling part 21 of the rotor 20.

The rotating unit 40 functions to cause the rotor 20 to protrude from or retract into the body 10 while being rotated when the body 10 is pushed or pulled back and forth, that is, when the body 10 is longitudinally moved after the bristles 35 of the brush assembly are disposed to be in contact with teeth.

The rotating unit 40 comprises the screw 41 and the rotation guide hole 43.

The screw 41 has a spiral rotation guide groove 42 longitudinally formed thereon, and the rotation guide hole 43 has a shape corresponding to the cross-section of the screw 41. Consequently, when the screw 41 disposed in the rotation guide hole 43 is moved back and forth, the screw 41 executes a rotational motion as well as the linear motion.

As described above, the automatic rotating interdental brush according to the present invention has a smaller number of components and a simpler structure compared to a conventional interdental brush.

In a manufacturing process of the automatic rotating interdental brush, the rotor 20 is inserted into the internal space 11 of the reception guide body 10A, and the screw 41 provided at the rear end of the rotor 20 is slightly inserted into the rotation guide hole 43 formed in the front end of the rotation guide body 10B. Subsequently, when the reception guide body 10A is pushed toward the rotation guide body 10B to be fitted on the rotation guide body 10B, the screw 41 is inserted into the rotation guide hole 43 while being rotated.

Consequently, the automatic rotating interdental brush according to the present invention can be manufactured at a lower cost and has higher productivity and competiveness.

As described above, the automatic rotating interdental brush according to the present invention can automatically rotate the brush only by slowly pushing and pulling the body even without the use of expensive components such as a battery and a motor and thus eliminates the need for cumbersome action of quickly reciprocating a brush up and down. Therefore, the automatic rotating interdental brush according to the present invention can efficiently clear away interdental extraneous substances, plaque and the like in convenient and prompt manner.

Furthermore, the automatic rotating interdental brush according to the present invention is composed of a smaller number of components and thus have a simpler structure, and the components can be quickly fabricated. Consequently, manufacturing costs are reduced and productivity is improved.

In addition, any of existing interdental brushes can be conveniently coupled to the front end of the rotor, and the brush can be replaced with a brush for ear cleaning so as to remove earwax.

Accordingly, the present invention is very useful in development of industry.

Although the automatic rotating interdental brush according to the present invention having the above-described configuration has been disclosed for illustrative purposes with reference to the accompanying drawings, those skilled in the art will appreciate that various modifications, additions and substitutions are possible, without departing from the scope and spirit of the invention as disclosed in the accompanying claims.

What is claimed is:

1. An automatic rotating interdental brush, comprising:
    a hollow cylindrical body having an internal space thereinside;
    a rotor slidably and rotatably received in the internal space, wherein the rotor includes at a front end thereof a coupling part to which a brush assembly is detachably attached, and includes at a rear end thereof a screw having a spiral rotation guide groove; and
    a rotation guide hole formed inside the hollow cylindrical body and having a shape corresponding to a cross-section of the screw, wherein the screw is inserted into the rotation guide hole so as to cause the screw to be automatically rotated along with the rotor and the brush assembly coupled thereto while the brush assembly moves linearly forward and backward when in use of the interdental brush,
    wherein the hollow cylindrical body comprises: a reception guide body having the internal space; and a rotation guide body coupled to a rear end of the reception guide body, the rotation guide hole being formed in a front end of the rotation guide body, and
    wherein the coupling part includes a plurality of inner surface sections having internal diameters that decrease in a stepwise fashion.

2. The automatic rotating interdental brush according to claim 1, wherein the reception guide body is provided at a front end thereof with an annular check protrusion, and the rotor is provided on an outer surface thereof with a shoulder that is caught by the annular check protrusion of the reception guide body thus preventing separation of the rotor.

3. The automatic rotating interdental brush according to claim 1, wherein the rotation guide body includes a reception space for reception and storage of a brush, and the rotation guide body is formed with a vent hole that allows the reception space to communicate with outside for ventilation of the reception space.

* * * * *